United States Patent
Ham et al.

[11] Patent Number: 6,143,900
[45] Date of Patent: Nov. 7, 2000

[54] STEREOSELECTIVE SYNTHESIS OF OXAZOLINE DERIVATIVE

[75] Inventors: Won Hun Ham, Seoul; Kyung Seok Choi, Kyunggi-Do; Han Won Lee, Seoul; Sung Ki Seo, Choongchungbuk-Do; Jin Kyu Park, Seoul; Ki Young Lee, Kyunggi-Do; Yong Hyun Kim, Seoul, all of Rep. of Korea

[73] Assignee: Dong Kook Pharmaceutical Co., Ltd., Seoul, Rep. of Korea

[21] Appl. No.: 09/426,778

[22] Filed: Oct. 26, 1999

[51] Int. Cl.⁷ .................................................. C07D 263/34
[52] U.S. Cl. ................................................... 548/236
[58] Field of Search ............................................. 548/236

[56] References Cited

U.S. PATENT DOCUMENTS

| | | | |
|---|---|---|---|
| 5,767,282 | 6/1998 | Gennari | 548/215 |
| 5,773,629 | 6/1998 | Yang et al. | 548/239 |
| 5,973,160 | 10/1999 | Poss et al. | 548/110 |

OTHER PUBLICATIONS

Deng et al., Total Synthesis of Alterobactin A, a Super Siderophore from an Open–Ocean Bacterium, J. Am. Chem. Soc., 1995, 117(29):7824–7825.

Kanazawa et al., Highly Stereocontrolled and Efficient Preparation of the Protected, Esterification–Ready Docetaxel (Taxotere) Side Chain, J. Org. Chem., 1994, 59(6):1238–1240.

Barco et al., A Chemoenzymatic Approach to Chiral Phenylisoerinates using 4–Isopropyl–2–Oxazolin–5–one as Masked Umpoled Synthon for Hydroxycarbonyl Anion, Tetrahedron Letters, 1994, 35(49):9289–9292.

Kingston et al., Synthesis of Taxol from Baccatin III via on Oxazoline Intermediate, Tetrahedron Letters, 1994, 35926):4483–4484.

Kearns & Kayser, Application of Yeast–Catalyzed Reductions to Synthesis of (2R,3S)–Phenylisoserine, Tetrahedron Letters, 1994, 35(18):2845–2848.

*Primary Examiner*—Deborah C. Lambkin
*Attorney, Agent, or Firm*—Kenyon & Kenyon

[57] ABSTRACT

The present invention relates to stereoselective synthetic method of oxazoline derivative. More particularly, it relates to a synthetic method of oxazoline derivative having the structure of formula I.

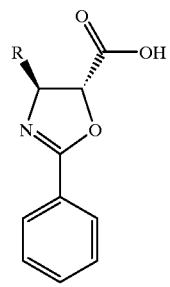

formula I wherein

R represents phenyl, benzyl, methyl, ethyl, isopropyl, isobutyl, cyclohexyl or cyclohexylmethyl.

4 Claims, No Drawings

STEREOSELECTIVE SYNTHESIS OF OXAZOLINE DERIVATIVE

BACKGROUND OF THE INVENTION

The present invention relates to a stereoselective synthetic method of oxazoline derivative. More particularly, it relates to a synthetic method of oxazoline derivative having the structure of formula I.

formula I

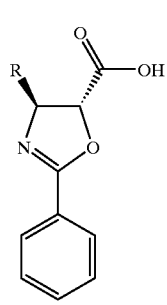

wherein
R represents phenyl, benzyl, methyl, ethyl, isopropyl, isobutyl, cyclohexyl or cyclohexylmethyl.

β-amino-α-hydroxy acid has been regarded as a HIV protease inhibitor or a component of physiologically active compound. Further, taxol having the structure of formula A has been known as an efficacious anti-cancer medicine. To express the anti-cancer effect of taxol, it has been known that 3-(N-benzoylamino)-2-hydroxy-3-phenylpropionic acid has to be placed at C-13 site of the taxol.

formula A

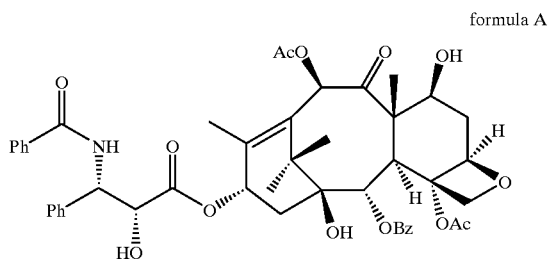

The crude taxan has been isolated from the plant. However, it is hard to extract it from plant, because only a small quantity of taxan exists in the plant. Meanwhile, the semi-synthetic process from baccatin III represented by formula B has been carried out, because baccatin III can be obtained in a desirable quantity from the plant. Therefore, the stereoselective synthetic method of β-amino-α-hydroxy acid which is essential chain of taxol has been regarded as very important method.

formula B

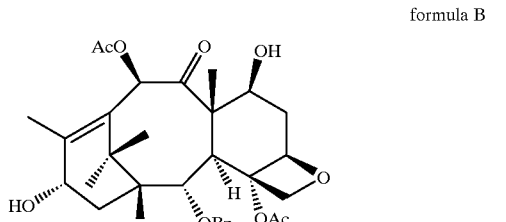

Such stereoselective synthetic methods of (β-amino-α-hydroxy acid have been reported in following documents;

Tetrahedron Letter, 35, pp 2845–2848 (1994); Tetrahedron Letter, 35, pp 9289–9292 (1994); J. Org. Chem., 59, pp 1238–1240 (1994); J. Am. Chem. Soc., 117, pp 7824–7825 (1995).

On the other hand, it has been reported that the binding reaction between hydroxy part C-13 site of baccatin III and 3-(N-benzoylamino)-2-hydroxy-3-phenylpropionic acid for preparing taxol requires severe reaction condition, and that the yield of such reaction is not quite well. To overcome such defect, the binding method using oxazoline derivative can be replaced by 3-(N-benzoylamino)-2-hydroxy-3-phenylpropionic acid [Tetrahedron Letter, 26, pp 4483–4484 (1994)].

Of course, taxol can be obtained by semi-synthetic method from baccatin III. However, the problem is how to obtain the highly purified synthetic taxol, because the purity of it affects the efficacy of taxol. Therefore, the development of synthetic method for oxazoline has important meaning due to the effect to the purity of taxol, as well as the role of intermediate of HIV protease inhibitor.

SUMMARY OF THE INVENTION

The object of the present invention is to provide a stereoselective synthetic method of oxazoline derivative equivalent to β-amino-α-hydroxy acid using the naturally existing amino acid as starting material.

The another object of the present invention is to provide a stereoselective synthetic method of oxazoline derivative to prepare taxol of formula A from baccatin III of formula B, and to afford the intermediate of HIV protease inhibitor.

The further object of the present invention is to provide a stereoselective synthetic method of oxazoline derivative comprising the following steps of;

i) cyclizing the compound of formula II in the presence of 0.02~0.1 mole % of palladium (Pd) catalyst at 20~50° C. by separating the leaving group X to obtain the compound of formula III; and ii) oxidizing the compound of formula III by adding the oxidizing agent in the mixed solvent (acetonitrile/carbontetrachloride/water) in the presence of ruthenium catalyst to obtain the compound of formula I.

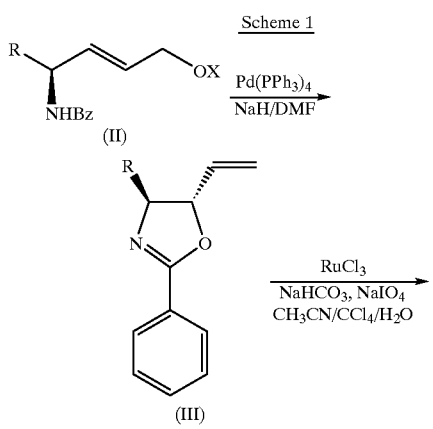

-continued

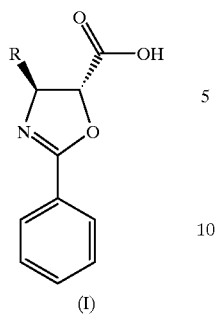

(I)

wherein

R represents phenyl, benzyl, methyl, ethyl, isopropyl, isobutyl, cyclohexyl or cyclohexylmethyl;

X represents acetyl, benzoyl or carbonate as leaving group.

Further, the palladium (Pd) catalyst is selected from the group consisting of tetrakistriphenylphosphine palladium; mixture of $Pd(OAc)_2$, $PdCl_2$ and $Ph_3P$; and mixture of dibenzylidene acetone palladium, dichlorodiphenyl palladium and hydrazine. The oxidizing agent is selected from the group consisting of sodium periodate($NaIO_4$); potassium periodate($KIO_4$); and potassium permanganate($KMnO_4$).

DETAILED DESCRIPTION OF THE INVENTION

The compound of formula II using the starting material of the present invention can be prepared from α-amino acid. The reaction scheme shows the preparation method of compound of formula II, which is prepared following steps of;

i) reducing α-amino acid (IV) to α-amino alcohol (V) using the reductant;

ii) oxidizing α-amino alcohol (V) to α-amino aldehyde (VI);

iii) reacting from α-amino aldehyde (VI) to 4-N-benzoylamino-4-phenyl-2-butenal (VII) using formylmethylenetriphenylphosphorane;

iv) reducing 4-N-benzoylamino-4-pheny-2-butenal (VII) to 4-N-benzoyl-amino-4-pheny-2-butenol (VIII); and v) converting 4-N-benzoylamino-4-pheny-2-butenol (VIII) into the starting material of oxazoline synthesis (II)

Scheme 2

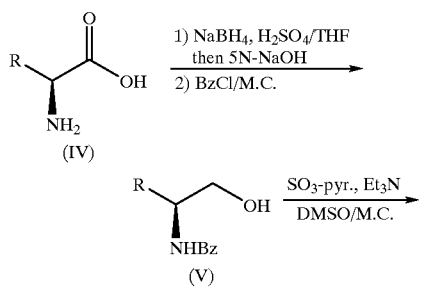

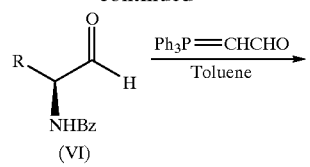

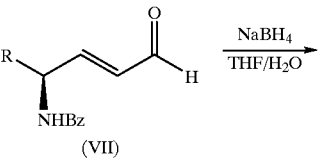

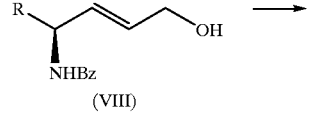

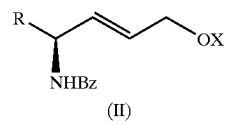

(II)

wherein

R is alkyl or aryl, for example, phenyl, benzyl, methyl, ethyl, isopropyl, isobutyl, cyclohexyl or cyclohexylmethyl;

X is acetyl, benzoyl or carbonate as leaving group;

Bz is benzoyl;

M. C. is methylene chloride;

Ph is phenyl;

pyr is pyridine;

THF is tetrahydrofuran; and

DMSO is dimethylsulfoxide.

The present invention can be explained more specifically as follows.

The preferred palladium (Pd) catalyst is tetrakistriphenylphosphine palladium or the mixture of $Pd(OAc)_2$, $PdCl_2$ and $Ph_3P$. Even though the mixture of dibenzylidene acetone palladium, dichlorodiphenyl palladium and hydrazine can be used, the tetrakistriphenylphosphine palladium is much desired. The quantity of palladium (Pd) catalyst is 0.02~0.1 mole %, desirably, 0.04~0.06 mole %.

The reaction can be carried out in the temperature range of 20~50° C., preferably, 22~28° C. DMF (dimethylformamide) can be selected as preferred solvent in case of using the tetrakistriphenylphosphine palladium catalyst. THF (tetrahydrofuran) or chloroform can be selected as preferred solvent in case of using the dibenzylidene acetone palladium catalyst. Further, DMF can be selected as preferred solvent in case of using the mixture of $Pd(OAc)_2$ and $Ph_3P$.

The reaction time requires 6~10 hours, preferably, 7~9 hours. Acetyl is the preferred leaving group represented by X among the acetyl, benzoyl and carbonate.

The reaction process for preparing compound of formula II can be explained more specifically as follows.

During the reduction reaction from α-amino acid (IV) to α-amino alcohol (V) using the reductant of $NaBH_4$, the molar ratio of $NaBH_4$ and sulfuric acid should be about 2:1. Further, the sulfuric acid used should be diluted by ether. The reaction temperature may be in the range of 0~20° C. when sulfuric acid is added. The time for adding sulfuric acid may be for 3~5 hours, whereas the reflux time using 5N-sodium hydroxide may be for 3~5 hours. The reaction temperature at the time of adding benzoylchloride is preferably about 0° C. having the addition velocity of 1.0~2.0 ml/min.

In the oxidation reaction from α-amino alcohol (V) to α-amino aldehyde (VI), solid type of sulfurtrioxide/pyridine should be added. Further, the reaction temperature is preferably about 0° C. The time for obtaining better yield may be for 2~3 hours.

In the reaction from α-amino aldehyde (VI) to 4-N-benzoylamino-4-phenyl-2-butenal (VII) using formylmethylenetriphenylphosphorane, the reaction temperature is 20~90° C., preferably, about 60° C. The reaction time may be for 1.5~2.5 hours. Further, benzene, toluene or chloroform can be used as reaction solvent.

In the reduction reaction from 4-N-benzoylamino-4-pheny-2-butenal (VII) to 4-N-benzoylamino-4-pheny-2-butenol (VIII), tetrahydofuran/water (9:1) is much preferred solvent. Further, the reaction time may be for 30 minutes. The reaction temperature is preferably 0~20° C.

4-N-benzoylamino-4-pheny-2-butenol (VIII) can be converted into the starting material of oxazoline synthesis by the reaction with acetic anhydride, benzoyl chloride or ethylchloroformate. The reaction time may be for 6~10 hours. The reaction temperature is preferably 0° C.~room temperature. The required quantity of acetic anhydride, benzoyl chloride or ethylchloroformate is 1.5~2.5 in an equivalent ratio, preferably, about 2.0 in an equivalent ratio.

(S)-(+)-phenylglycine and L-phenylalanine are exemplified as starting material in the following examples, but the synthesis of the oxazoline derivative (I) in this invention comprises all amino acids as starting material without limitation.

The present invention will be more specifically explained by the following examples. However, it should be understood that the examples are intended to illustrate but not in any manner to limit the scope of the present invention.

EXAMPLE 1
Synthesis of the Compound (V)

N-benzoylphenylglycinol is synthesized by following steps of: i) suspending 1 mole (151 g) of (S)-(+)-phenylglycine to 1 L of tetrahydrofuran, ii) adding 2.5 mole (100 g) of $NaBH_4$ to the solution, iii) dropping 1.25 mole of ether-diluted sulfuric acid (66 ml, total volume 200 ml) to the solution at 0° C., iv) after reacting the solution for 12 hours at room temperature, adding 200 ml of methanol slowly, v) after adding 1 L of 5N-NaOH, evaporating organic solvent and refluxing for 3 hours, vi) after cooling to room temperature, adding 1 L of methylenechloride to the solution, vii) adding 1 mole of benzoylchloride to the solution slowly at 0° C., viii) after finishing the reaction, filtering the reaction mixture, ix) washing the product with hot water three times, and x) obtaining 195 g (81%) of N-benzoylphenylglycinol after drying the product.

$^1$H-NMR(DMSO-$d_6$) 3.67(dd, 1H), 4.96(t, 1H), 5.06(dd, 1H), 7.20–7.55(m, 8H), 7.90(m, 2H), 8.72(d, 1H)

EXAMPLE 2
Synthesis of the Compound (VI)

N-benzoylaminoaldehyde is synthesized by following steps of: i) suspending 0.1 mole (24.1 g) of N-benzoylphenylglycinol to 100 ml of methylenechloride/methylsulfoxide (5:1), ii) after cooling to 0° C., adding 31.8 g (0.2 mole) of sulfurtrioxide-pyridine to the solution, iii) after adding 55 ml (0.4 mole) of triethylamine, agitating the solution for 2 hours, iv) after finishing the reaction, adding 200 ml of ethylacetate to the reaction mixture, v) washing the reaction mixture with 100 ml of water and 100 ml of saturated $NH_4Cl$ solution, vi) drying the reaction mixture with magnesium sulfate, and vii) obtaining 21 g (87%) of crude N-benzoylaminoaldehyde after filtering and drying the product.

$^1$H-NMR(CDCl$_3$) 4.80(br, 1H), 6.19(d, 1H), 7.23–7.87 (m, 10H), 9.83(s, 1H)

EXAMPLE 3
Synthesis of the Compound (VII)

4-N-benzoylamino-4-phenyl-2-butenal is synthesized by following steps of: i) adding 100 ml of toluene to 21 g (0.087 mole) of N-benzoylphenylglycinealdehyde, ii) after adding 34 g (0.11 mole) of formylmethylenetriphenylphosphorane, refluxing the solution for 2 hours, iii) after finishing the reaction, drying the reaction mixture, and iv) obtaining 13.8 g (60%) of 4-N-benzoylamino-4-phenyl-2-butenal after isolating the product using column chromatography (hexane:ethylacetate=1:1).

EXAMPLE 4
Synthesis of the Compound (VIII)

4-N-benzoylamino-4-phenyl-2-butenol is synthesized by following steps of: i) adding 50 ml of tetrahydrofuran/water (9:1) to 13.3 g (0.05 mole) of 4-N-benzoylamino-4-phenyl-2-butenal, ii) after adding 1.9 g (0.05 mole) of $NaBH_4$, agitating the solution for 30 minutes, iii) after adding 30 ml of 1N-HCl, extracting the reaction mixture with 50 ml of ether, iv) drying the reaction mixture with magnesium sulfate, and v) obtaining 13.6 g of crude 4-N-benzoylamino-4-phenyl-2-butenol after filtering the product.

EXAMPLE 5
Synthesis of the Compound (II)

1-acetoxy-4-N-benzoylamino-4-phenyl-2-butene is synthesized by following steps of: i) adding 20 ml of pyridine to 13.6 g (0.05 mole) of 4-N-benzoylamino-4-phenyl-2-butenol, ii) after adding 10.2 g (0.1 mole) of acetic anhydride, agitating the solution for 4 hours, iii) after finishing the reaction, adding 50 ml of methylene chloride, iv) washing the reaction mixture with 50 ml of 1N-HCl and 50 ml of saturated $NaHCO_3$ solution, and v) obtaining 14.7 g (95%) of 1-acetoxy-4-N-benzoylamino-4-phenyl-2-butene after recrystallizing the product using the solvent of hexane/ethylacetate (2:1).

$^1$H-NMR(CDCl$_3$) 2.08(s, 3H), 4.63(d, 2H), 5.82(dt, 1H), 5.89(dd, 1H), 6.04(dd, 1H), 6.4(br, 1H), 7.32–7.53(m, 8H), 7.79(m, 2H)

Other leaving groups can be synthesized using benzoylchloride or methylchloroformate as the same manners described in the above.

EXAMPLE 6
Synthesis of the Compound (V)

N-benzoylphenylalaninol is synthesized by following steps of: i) suspending 1 mole (163 g) of L-phenylalaninol to 1 L of tetrahydrofuran, ii) adding 2.5 mole (100 g) of $NaBH_4$ to the solution, iii) dropping 1.25 mole of ether-diluted sulfuric acid (66 ml, total volume 200 ml) to the solution at 0° C., iv) after reacting the solution for 12 hours at room temperature, adding 200 ml of methanol slowly, v) after adding 1 L of 5N-NaOH, evaporating organic solvent and refluxing for 3 hours, vi) after cooling to room temperature, adding 1 L of methylenechloride to the solution, vii) adding 1 mole of benzoylchloride to the solution slowly at 0° C., viii) after finishing the reaction, filtering the reaction mixture, ix) washing the product with hot water three times, and x) obtaining 207 g (81%) of N-benzoylphenylalaninol after drying the product.

$^1$H-NMR(DMSO-$d_6$) δ 2.79(dd, 1H), 2.94(dd, 1H), 3.45 (m, 2H), 4.14(m, 1H), 4.87(bt,1H), 7.13–7.51(m, 8H), 7.77 (d, 2H), 8.18(d, 1H)

EXAMPLE 7
Synthesis of the Compound (VI)

N-benzoylaminoaldehyde is synthesized by following steps of: i) suspending 0.1 mole (25.5 g) of N-benzoylphenylalaninol to 100 ml of methylenechloride/methylsulfoxide (5:1), ii) after cooling to 0° C., adding 31.8 g (0.2 mole) of sulfurtrioxide-pyridine to the solution, iii) after adding 55 ml (0.4 mole) of triethylamine, agitating the solution for 2 hours, iv) after finishing the reaction, adding 200 ml of ethylacetate to the reaction mixture, v) washing the reaction mixture with 100 ml of water and 100 ml of saturated $NH_4Cl$ solution, vi) drying the reaction mixture with magnesium sulfate, and vii) obtaining 22 g (87%) of crude N-benzoylaminoaldehyde after filtering and drying the product.

$^1$H-NMR($CDCl_3$) δ 3.32(m, 2H), 4.93(dd, 1H), 6.71(m, 1H), 7.20–7.72(m, 8H), 7.74(d, 2H), 9.74(s, 1H)

EXAMPLE 8
Synthesis of the Compound (VII)

4-N-benzoylamino-5-phenyl-2-pentenal is synthesized by following steps of: i) adding 100 ml of toluene to 22 g (0.087 mole) of N-benzoylphenylalaninaldehyde, ii) after adding 34 g (0.11 mole) of formylmethylenetriphenylphosphorane, refluxing the solution for 2 hours, iii) after finishing the reaction, drying the reaction mixture, and iv) obtaining 14.6 g (60%) of 4-N-benzoylamino-5-phenyl-2-pentenal after isolating the product using column chromatography (hexane:ethylacetate=1:1).

$^1$H-NMR($CDCl_3$) δ 3.12(m, 2H), 5.22(m, 1H), 6.20(dd, 1H), 6.83(dd, 1H), 7.20–7.77(m, 10H), 9.49(d, 1H)

EXAMPLE 9
Synthesis of the Compound (VII)

4-N-benzoylamino-5-phenyl-2-pentenol is synthesized by following steps of: i) adding 50 ml of tetrahydrofuran/water (9:1) to 14.0 g (0.05 mole) of 4-N-benzoylamino-5-phenyl-2-pentenal, ii) after adding 1.9 g (0.05 mole) of $NaBH_4$, agitating the solution for 30 minutes, iii) after adding 30 ml of 1N-HCl, extracting the reaction mixture with 50 ml of ether, iv) drying the reaction mixture with sodium sulfate, and v) obtaining 14.06 g of crude 4-N-benzoylamino-5-phenyl-2-pentenol after filtering the product.

EXAMPLE 10
Synthesis of the Compound (II)

1-acetoxy-4-N-benzoylamino-5-phenyl-2-pentene is synthesized by following steps of: i) adding 20 ml of pyridine to 14.6 g (0.05 mole) of 4-N-benzoylamino-5-phenyl-2-pentenol, ii) after adding 10.2 g (0.1 mole) of acetic anhydride, agitating the solution for 4 hours, iii) after finishing the reaction, adding 50 ml of methylene chloride, iv) washing the reaction mixture with 50 ml of 1N-HCl and 50 ml of saturated $NaHCO_3$ solution, and v) obtaining 15.36 g (95%) of 1-acetoxy-4-N-benzoylamino-5-phenyl-2-pentene after recrystallizing the product using the solvent of hexane/ethylacetate (2:1).

$^1$H-NMR δ 2.05(s, 3H), 3.00(dd, 2H), 4.54(d, 2H), 5.02 (m, 1H), 5.70(dt,1H), 5.84(dd, 1H), 7.22–7.49(m, 8H), 7.67–7.69(m, 2H)

Other leaving groups can be synthesized using benzoylchloride or methylchloroformate as the same manners described in the above.

EXAMPLE 11
Synthesis of the Compound (III)

(4S-trans)4,5-dihydro-2,4-diphenyl-5-vinyl-oxazoline is synthesized by following steps of: i) suspending 15.6 mg (0.65 mmole) of sodium hydride to 2 ml of DMF (dimethylformamide), ii) dropping 200 mg (0.65 mmole) of 1-acetoxy-4-N-benzoylamino-4-phenyl-2-butene dissolved in 1 ml of DMF to the solution at 0° C., iii) adding 38.1 mg (0.033 mmole) of tetrakistriphenylphosphine palladium, iv) after agitating the solution for 8 hours, finishing the reaction, v) after adding 20 ml of ethylacetate, washing the product with 4 ml of distilled water five times and 20 ml of brine once, vi) after drying the reaction mixture with magnesium sulfate, filtering the reaction mixture, and vii) obtaining 84.3 mg (52%, 100% de) of (4S-trans)-4,5-dihydro-2,4-diphenyl-5-vinyl-oxazoline after isolating the product using column chromatography (hexane:ethylacetate=6:1).

$^1$H-NMR($CDCl_3$) 4.88(dd, J=7.0, 8.0 Hz, 1H), 5.05(d, J=8.0 Hz, 1H), 5.33(d, J=10.5 Hz, 1H), 5.38(d, J=17.5 Hz, 1H), 6.09(ddd, J=7.0, 10.5, 17.5 Hz, 1H), 7.31–7.53(m, 8H), 8.08(m, 2H)

EXAMPLE 12
Synthesis of the Compound (III)

(4S-trans)-4,5-dihydro-2-phenyl-4-benzyl-5-vinyl-oxazoline is synthesized by following steps of: i) suspending 15 mg (0.61 mmole) of sodium hydride to 2 ml of DMF, ii) dropping 200 mg (0.61 mmole) of 1-acetoxy-4-N-benzoylamino-5-phenyl-2-pentene dissolved in 1 ml of DMF to the solution at 0° C., iii) adding 36 mg (0.03 mmole) of tetrakistriphenylphosphine palladium, iv) after agitating the solution for 8 hours, finishing the reaction, v) after adding 20 ml of ethylacetate, washing the product with 4 ml of distilled water five times and 20 ml of brine once, vi) after drying the reaction mixture with magnesium sulfate, filtering the reaction mixture, and vii) obtaining 79 mg (53%, 60% de) of (4S-trans)4,5-dihydro-2-phenyl-4-benzyl-5-vinyl-oxazoline after isolating the product using column chromatography (hexane:ethylacetate=4:1).

$^1$H-NMR δ2.79(dd, J=7.5, 13 Hz, 1H), 3.26(dd, J=5.5, 13 Hz, 1H), 4.26(ddd, J=5.5, 7.0, 7.5 Hz, 1H), 4.76(dd, J=6.5, 7.0 Hz, 1H), 5.06(dd, 2H), 5.72(ddd, 1H), 7.22–7.51(m, 8H), 7.97–8.01(m, 2H)

EXAMPLE 13
Synthesis of the Compound (III)

(4S-trans)-4,5-dihydro-2-phenyl-4-isopropyl-5-vinyl-oxazoline is synthesized by following steps of: i) suspending 15.6 mg (0.65 mmole) of sodium hydride to 2 ml of DMF, ii) dropping 200 mg (0.65 mmole) of 1-acetoxy-4-N-benzoylamino-6-methyl-2-heptene dissolved in 1 ml of DMF to the solution at 0° C., iii) adding 38.1 mg (0.033 mmole) of tetrakistriphenylphosphine palladium, iv) after agitating the solution for 8 hours, finishing the reaction, v) after adding 20 ml of ethylacetate, washing the product with 4 ml of distilled water five times and 20 ml of brine once, vi) after drying the reaction mixture with magnesium sulfate, filtering the reaction mixture, and vii) obtaining 84.3 mg (61%, 58% de) of (4S-trans)4,5-dihydro-2-phenyl-4-isopropyl-5-vinyl-oxazoline after isolating the product using column chromatography (hexane:ethylacetate=6:1).

Table 1 shows the yield of intramolecular cyclizing reaction using palladium catalyst in R groups and leaving groups.

TABLE 1

|   |           | leaving group (X) | | |
|---|-----------|---------|---------|------------------|
|   |           | acetyl  | benzoyl | methyl carbonate |
| R | phenyl    | 52%     | 35%     | 37%              |
|   | benzyl    | 53%     | 37%     | 39%              |
|   | isopropyl | 61%     | 39%     | 43%              |

EXAMPLE 14

Synthesis of the Compound (I)

(4S-trans)4,5-dihydro-2,4-diphenyl-5-carboxylate methyl ester is synthesized by following steps of: i) adding 124.6 mg (0.5 mmole) of (4S-trans)-4,5-dihydro-2,4-diphenyl-5-vinyl-oxazoline to 10 ml of mixture of acetonitrile/carbontetrachloride/water (1:1:1) agitated in room temperature, ii) after adding 273 mg (3.25 mmole) of sodium bicarbonate and 588 mg (5.75 mmole) of sodium periodate to the solution, agitating the solution for 5 minutes, iii) adding catalytic amount (about 1 mg) of ruthenium chloride, agitating the solution for 2 days, iv) after finishing the reaction, extracting the reaction mixture with ether, v) acidifying the reaction mixture with 1N-HCl, vi) obtaining 105.5 mg (53%, 100% de) of (4S-trans)-4,5-dihydro-2,4-diphenyl-5-carboxylic acid after extracting the reaction mixture with methylenechloride, vii) after adding 10 ml of ether to compound of vi), methylesterifying by adding diazomethane, and viii) obtaining 110 mg of (4S-trans)4,5-dihydro-2,4-diphenyl-5-carboxylate methyl ester after evaporating ether.

$^1$H-NMR(CDCl$_3$) 3.84(s, 3H), 4.91(d, J=6.5 Hz, 1H), 5.45(d, J=6.5 Hz, 1H), 7.29–7.57(m, 8H), 8.08(m, 2H)

EXAMPLE 15

Synthesis of the Compound (I)

(4S-trans)4,5-dihydro-2-phenyl-4-benzyl-carboxylic acid is synthesized by following steps of: i) adding 138.6 mg (0.5 mmole) of (4S-trans)4,5-dihydro-2-phenyl-4-benzyl-5-vinyl-oxazoline to 10 ml of mixture of acetonitrile/carbontetrachloride/water (1:1:1) agitated in room temperature, ii) after adding 273 mg (3.25 mmole) of sodium bicarbonate and 588 mg (5.75 mmole) of sodium periodate to the solution, agitating the solution for 5 minutes, iii) adding catalytic amount (about 1 mg) of ruthenium chloride, agitating the solution for 2 days, iv) after finishing the reaction, extracting the reaction mixture with ether, v) acidifying the reaction mixture with 1N-HCl, and vi) obtaining 95.6 mg (68%) of (4S-trans)-4,5-dihydro-2-phenyl-4-benzyl-5-carboxylic acid after extracting the reaction mixture with methylenechloride.

What is claimed is:

1. A stereoselective synthetic method of oxazoline derivative comprising the steps of;

i) cyclizing the compound of formula II in the presence of 0.02~0.1 mole % of palladium (Pd) catalyst at 20~50° C. by separating the leaving group X to obtain the compound of formula III; and ii) oxidizing the compound of formula III by adding the oxidizing agent in the mixed solvent (acetonitrile/carbontetrachloride/water) in the presence of ruthenium catalyst to obtain the compound of formula I

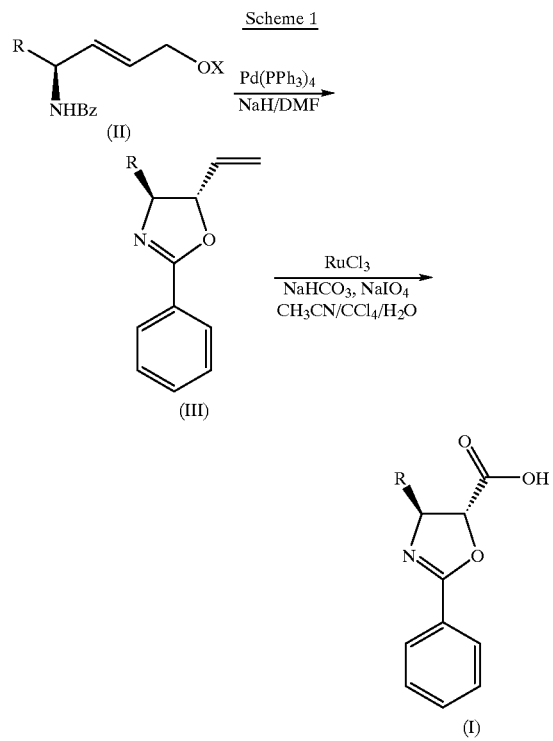

Scheme 1 wherein

R represents phenyl, benzyl, methyl, ethyl, isopropyl, isobutyl, cyclohexyl or cyclohexylmethyl;

X represents acetyl, benzoyl or carbonate as leaving group.

2. The stereoselective synthetic method of oxazoline derivative according to claim 1, wherein the palladium (Pd) catalyst is selected from the group consisting of tetrakistriphenylphosphine palladium; mixture of Pd(OAc)$_2$, PdCl$_2$ and Ph$_3$P; and mixture of dibenzylidene acetone palladium, dichlorodiphenyl palladium and hydrazine.

3. The stereoselective synthetic method of oxazoline derivative according to claim 1, wherein the oxidizing agent is selected from the group consisting of sodium periodate (NaIO$_4$); potassium periodate(KIO$_4$); and potassium permanganate (KMnO$_4$).

4. The stereoselective synthetic method of oxazoline derivative according to claim 1, wherein the compound of formula II is prepared following steps of;

i) reducing α-amino acid (IV) to α-amino alcohol (V) using the reductant;

ii) oxidizing α-amino alcohol (V) to α-amino aldehyde (VI);

iii) reacting from α-amino aldehyde (VI) to 4-N-benzoylamino-4-phenyl-2-butenal (VII) using formylmethylenetriphenylphosphorane;

iv) reducing 4-N-benzoylamino-4-pheny-2-butenal (VII) to 4-N-benzoyl-amino-4-pheny-2-butenol (VIII); and v) converting 4-N-benzoylamino-4-pheny-2-butenol (VIII) into the starting material of oxazoline synthesis (II)

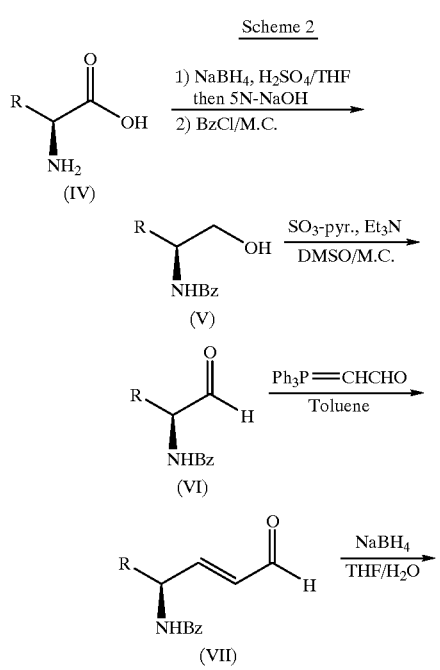
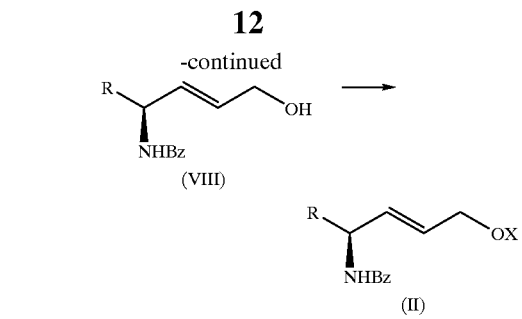
wherein
R is alkyl or aryl, for example, phenyl, benzyl, methyl, ethyl, isopropyl, isobutyl, cyclohexyl or cyclohexylmethyl;
X is acetyl, benzoyl or carbonate as leaving group;
Bz is benzoyl;
M. C. is methylene chloride
Ph is phenyl;
pyr is pyridine
THF is tetrahydrofuran; and
DMSO is dimethylsulfoxide.
\* \* \* \* \*